United States Patent
Kim et al.

(10) Patent No.: US 11,433,384 B2
(45) Date of Patent: Sep. 6, 2022

(54) NITROGEN-DOPED CATALYST FOR OXIDATIVE COUPLING REACTION OF METHANE, MANUFACTURING METHOD OF NITROGEN-DOPED CATALYST FOR OXIDATIVE COUPLING REACTION OF METHANE THEREBY, AND METHOD FOR OXIDATIVE COUPLING REACTION OF METHANE USING THE SAME

(71) Applicant: KOREA INSTITUTE OF ENERGY RESEARCH, Daejeon (KR)

(72) Inventors: Hee-yeon Kim, Daejeon (KR); Tae-woo Kim, Daejeon (KR); Ji-haeng Yu, Daejeon (KR); Dae Keun Lee, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 13 days.

(21) Appl. No.: 16/953,929

(22) Filed: Nov. 20, 2020

(65) Prior Publication Data

US 2022/0161249 A1 May 26, 2022

(51) Int. Cl.
| | |
|---|---|
| *B01J 37/04* | (2006.01) |
| *B01J 23/34* | (2006.01) |
| *B01J 21/08* | (2006.01) |
| *B01J 37/08* | (2006.01) |
| *B01J 6/00* | (2006.01) |
| *B01J 35/00* | (2006.01) |
| *C07C 2/84* | (2006.01) |
| *B01J 31/02* | (2006.01) |
| *B01J 27/053* | (2006.01) |

(52) U.S. Cl.
CPC .............. *B01J 37/04* (2013.01); *B01J 6/001* (2013.01); *B01J 21/08* (2013.01); *B01J 23/34* (2013.01); *B01J 27/053* (2013.01); *B01J 31/0244* (2013.01); *B01J 35/0006* (2013.01); *B01J 37/08* (2013.01); *C07C 2/84* (2013.01)

(58) Field of Classification Search
CPC ... B01J 37/04; B01J 37/08; B01J 6/001; B01J 21/08; B01J 31/0244; B01J 35/0006; C07C 2/84
See application file for complete search history.

(56) References Cited

U.S. PATENT DOCUMENTS 7,902,133 B2    3/2011  Devlin et al.

FOREIGN PATENT DOCUMENTS

| KR | 10-2010-0130722 A | 12/2010 |
| KR | 10-2018-0113448 A | 10/2018 |

OTHER PUBLICATIONS

Liu et al., Journal of Natural Gas Chemistry, (2008), 17(1), p. 59-63.*
Lv et al., "Selectively nitrogen-doped carbon materials as superior metal-free catalysts for oxygen reduction", Nature Communications, Aug. 23, 2018, 2018(9), pp. 1-11.

* cited by examiner

*Primary Examiner* — Yong L Chu
(74) *Attorney, Agent, or Firm* — Birch, Stewart, Kolasch & Birch, LLP

(57) ABSTRACT

A nitrogen-doped catalyst for oxidative coupling of methane, which is a catalyst for obtaining a C2 hydrocarbon product with high yield, and a method for manufacturing the catalyst are provided. An embodiment of the present inventive concept relates to a nitrogen-doped catalyst for oxidative coupling of methane having a silica support; and sodium tungstate and manganese supported on the support.

6 Claims, 8 Drawing Sheets

NITROGEN-DOPED CATALYST FOR OXIDATIVE COUPLING REACTION OF METHANE, MANUFACTURING METHOD OF NITROGEN-DOPED CATALYST FOR OXIDATIVE COUPLING REACTION OF METHANE THEREBY, AND METHOD FOR OXIDATIVE COUPLING REACTION OF METHANE USING THE SAME

BACKGROUND OF THE INVENTION

1. Field of the Invention

The present inventive concept relates to a nitrogen-doped catalyst for an oxidative coupling reaction of methane and a method for manufacturing this catalyst, and more particularly, the invention relates to a method for manufacturing a nitrogen-doped catalyst for an oxidative coupling reaction of methane, the method including a step of doping nitrogen into a $Na_2WO_4/Mn/SiO_2$ catalyst using pyridine, and a nitrogen-doped catalyst for an oxidative coupling reaction of methane produced by the above-described method.

2. Description of the Related Art

Under the recent circumstances in which exploitation of new energy sources is urgently needed due to the depletion of fossil fuels and a rapid increase in energy consumption, shale gas is attracting attention as a new raw material for energy and petroleum chemical products along with a reduction in the cost resulting from the development of mining technologies. Shale gas contains a large quantity of methane, and if the main component methane could be converted to ethane or ethylene, both of which have higher added values, shale gas would have enormous potentiality as a raw material to be supplied for chemical products and fuel production.

Methods for converting methane into ethane or ethylene include direct conversion processes and indirect conversion processes, and existing technologies imply "indirect conversion processes" of going through several complicated stages under high temperature and high pressure. In contrast, a technology for directly producing ethane or ethylene from methane through a single process is referred to as "direct conversion process", and a representative example of the direction conversion method is oxidative coupling of methane (OCM). This is a method useful for obtaining a C2 (having two carbon atoms) hydrocarbon such as ethane or ethylene from methane, which is a main raw material of natural gas. The following Reaction Formula 1 represents a reaction formula by which methane is converted to ethylene, which is one of C2 hydrocarbons through an oxidative coupling reaction.

$2CH_4 + O_2 \rightarrow C_2H_4 + 2H_2O$ <Reaction Formula 1>

An oxidative coupling reaction of methane as described above has an advantage that C2 hydrocarbons can be obtained by a relatively simple reaction system without any additional process or treatment process. $Na_2WO_4/Mn/SiO_2$ catalysts are known as catalysts that are highly stable and effective for an oxidative coupling process of methane, and these catalysts were first reported by Fang et al. in 1992 (X. Fang, S. Li, J. Lin, Y. Chu, "Oxidative coupling of methane on W—Mn catalysts," J. Mol. Catal. (China), 6(1992), pp. 427-433). However, the oxidative coupling reaction of methane is a reaction of cleaving the strong C—H bond and is a reaction that requires high heat of reaction. Therefore, activation of methane through an oxidative coupling reaction of methane generally requires a temperature of 800° C. or higher. Furthermore, the oxidative coupling reaction of methane is an exothermic reaction and has a problem in the process, in which hot spots are generated around a catalyst layer, and these hot spots are generated more severely as the reaction activity is higher. Such undesired temperature increase not only adversely affects the catalyst but also lowers the selectivity for the C2 product.

In order to increase the yield of a C2 product produced by the oxidative coupling reaction of methane, the conversion ratio of methane and the selectivity of the C2 product should be increased simultaneously. In order to increase the conversion ratio of methane, a high temperature and a high oxygen partial pressure (being rich in oxygen) are needed. However, in this case, the reaction proceeds along a thermodynamically stable reaction path of producing CO or $CO_2$, and this causes lowering of the selectivity of the product.

To date, catalysts obtained by supporting sodium tungstate-manganese oxide on a metal oxide such as silica ($SiO_2$) are used for the oxidative coupling reaction of methane. For example, Korean Unexamined Patent Publication No. 2018-0113448 relates to a silica-supported sodium tungstate catalyst with added metals, a method for manufacturing this catalyst, and a method of performing an oxidative coupling reaction of methane using this catalyst. It is disclosed in the patent document that by supporting catalyst components including sodium tungstate and one or more metals selected from the group consisting of aluminum, magnesium, zinc, copper, cobalt, cerium, lanthanum, nickel, lithium, chromium, and manganese on a silicon carrier, the conversion ratio of methane and the selectivity for the C2 hydrocarbon compound are increased, and thus the oxidative coupling reactivity of methane can be enhanced. Furthermore, Korean Unexamined Patent Publication No. 2010-130722 relates to a silica aerogel-supported catalyst and a method for conversing methane using this catalyst, and the patent document discloses a silica aerogel-supported catalyst including a silica aerogel carrier and sodium tungstate and manganese oxide supported in the carrier. However, nothing has been hitherto mentioned about a method for manufacturing a catalyst for oxidative coupling of methane, the method including a step of doping nitrogen into a $Na_2WO_4/Mn/SiO_2$ catalyst using pyridine, and a nitrogen-doped catalyst for oxidative coupling of methane produced by this method.

Thus, the inventors of the present inventive concept conducted an investigation to overcome the above-described problems of the related art technologies, and the inventors found that in a case in which a catalyst for oxidative coupling of methane is produced by doping nitrogen (N) into a $Na_2WO_4/Mn/SiO_2$ catalyst using pyridine in order to maximize the conversion ratio of methane and the selectivity for a C2 product, activation of methane can be increased by inducing the formation of oxygen vacancies in the catalyst, and in a case in which a low-temperature oxidative coupling reaction of methane is carried out using the above-described nitrogen-doped catalyst at a reaction temperature of 700° C., which is significantly lower than the general temperature for the oxidative coupling reaction of methane of 800° C. or higher, the reaction conversion ratio and the selectivity for a C2 product can be maximized so that consequently, a C2 hydrocarbon can be obtained with high yield. Thus, the inventors completed the present inventive concept.

SUMMARY OF THE INVENTION

A main object of the present inventive concept is to provide a method for manufacturing a nitrogen-doped catalyst for oxidative coupling of methane, which is a catalyst that increases activation of methane by inducing the formation of oxygen vacancies of the catalyst, which is an important factor of increasing the reaction activity, through nitrogen doping into the surface of a catalyst for oxidative coupling of methane, accordingly maximizes the reaction conversion ratio, and increases the selectivity for a product, whereby a C2 hydrocarbon product can be finally obtained with high yield; and a nitrogen-doped catalyst for oxidative coupling of methane produced by this method.

Another object of the present inventive concept is to provide a method for performing an oxidative coupling reaction of methane using a nitrogen-doped catalyst for oxidative coupling of methane produced by the production method described above.

According to an aspect of the present inventive concept, the present inventive concept provides a method for manufacturing a catalyst for oxidative coupling of methane, the method including a first step of preparing amorphous silica (amorphous $SiO_2$) as a support; a second step of adding and mixing an aqueous solution of manganese into the silica and drying the mixture to produce a catalyst having manganese oxide supported on silica; a third step of adding and mixing a pyridine solution into the catalyst of the second step and then drying the mixture to produce a catalyst having pyridine and manganese supported thereon; a fourth step of adding and mixing an aqueous solution of sodium tungstate into the catalyst of the third step and then drying the mixture to produce a catalyst having sodium tungstate, pyridine, and manganese supported thereon; and a fifth step of calcining the catalyst of the fourth step and obtaining a nitrogen-doped catalyst for oxidative coupling of methane.

Regarding a direction conversion method for methane, a $Na_2WO_4/Mn/SiO_2$ catalyst that is generally used for an oxidative coupling reaction of methane is known as an effective and highly stable catalyst; however, the catalyst has a problem of having low C2 selectivity and resulting in inefficient reactions. Thus, the present inventors found that in a case in which nitrogen is doped into a $Na_2WO_4/Mn/SiO_2$ catalyst using pyridine in order to increase the yield of a C2 produced by an oxidative coupling reaction of methane, activation of methane can be increased by inducing the formation of oxygen vacancies of the catalyst, and the reaction conversion ratio can be maximized. Thus, the inventors completed the present inventive concept.

According to the method for manufacturing a catalyst for oxidative coupling of methane of the present inventive concept, the aqueous solution of manganese of the second step is produced by dissolving a manganese precursor in distilled water and mixing the solution with silica such that the mass ratio of the manganese oxide in the catalyst for oxidative coupling of methane is 0.5 wt % to 5 wt %.

According to the method for manufacturing a catalyst for oxidative coupling of methane of the present inventive concept, the aqueous solution of pyridine of the third step is produced by mixing ethanol and pyridine at a volume ratio of 5 to 7:0.2 to 2.5, and preferably, a catalyst having pyridine and manganese supported thereon can be produced by mixing ethanol and pyridine at a volume ratio of 6.8:0.2, 6.5:0.5, 6:1, or 5:2 to produce an aqueous solution of pyridine, and then supporting this aqueous solution on the catalyst having a manganese component supported thereon.

According to the method for manufacturing a catalyst for oxidative coupling of methane of the present inventive concept, the aqueous solution of sodium tungstate of the fourth step is produced by dissolving a sodium tungstate precursor in distilled water and mixing the solution with the catalyst of the third step such that the mass ratio of sodium tungstate in the catalyst for oxidative coupling of methane is 2 wt % to 10 wt %.

According to the Test Examples of the present inventive concept, it can be verified that when the mass ratio of manganese oxide is 2.0 wt %, and the mass ratio of sodium tungstate is 5 wt %, activation of methane and conversion into C2 are easily achieved, and the maximum catalyst activity is obtained.

According to the method for manufacturing a catalyst for oxidative coupling of methane of the present inventive concept, drying in the second step through the fourth step is carried out for 12 to 24 hours at 100° C. to 120° C. In a case in which the drying temperature is lower than this temperature, or the drying time is not as sufficient as 12 hours or longer, the water used for supporting catalyst components is not completely removed, and there may be a problem such as lowered catalyst dispersibility or the like. On the other hand, in a case in which the drying temperature is higher than 120° C., the rate of drying may be so fast that the dispersibility of the catalyst components is lowered, and in a case in which the drying temperature is higher than this, a phenomenon of aggregation of catalyst materials may occur during the drying process.

According to the method for manufacturing a catalyst for oxidative coupling of methane of the present inventive concept, calcination of the fifth step is carried out by introducing the catalyst placed in an alumina crucible into a heating furnace in an air atmosphere, subsequently raising the temperature up to 750° C. to 900° C. at a rate of temperature increase of 10° C./min, and then maintaining the temperature for 4 to 6 hours, and thereby the catalyst is calcined to have catalytic properties suitable for an oxidative coupling reaction of methane.

According to the Test Example of the present inventive concept, in a case in which the calcination is carried out at a temperature of 800° C., the temperature was effective for crystallizing the support and forming a catalytically active phase, and in a case in which calcination is carried out a temperature lower than this, crystallization of the support or formation of the catalytically active phase is incompletely achieved so that the catalytic performance may be deteriorated. For a direction conversion reaction of methane, the reaction proceeds smoothly when the amorphous silica is converted to a crystalline α-cristobalite phase, and in a case in which calcination is carried out at a temperature lower than 800° C., crystallization of such a support does not occur sufficient.

According to an Experimental Example of the present inventive concept, an X-ray diffraction analysis was carried out in order to check what structural influence is exerted on the catalyst by nitrogen doping using pyridine in the method for manufacturing a catalyst for oxidative coupling of methane of the present inventive concept. As a result, in the case of a $Na_2WO_4$—$Mn/SiO_2$ catalyst that had not been treated with pyridine (Comparative Example 1), a $Na_2WO_4$ peak, an α-cristobalite peak (2θ=22.0°), and a manganese peak were confirmed, whereas in a $Na_2WO_4$—(PYD)-$Mn/SiO_2$ catalyst that had been doped with nitrogen using pyridine, it was confirmed that a $Na_4WO_5$ peak (2θ=17.5°) appeared (see Experimental Example 1 and FIG. 1). These results suggest that a pyridine treatment causes a change in the oxygen species of a metal oxide and consequently induces the formation of oxygen vacancies of the catalyst as a result of the change in the oxygen species of the catalyst, and such oxygen vacancies can play an important role of promoting activation of methane.

Furthermore, according to an Experimental Example of the present inventive concept, an X-ray photoelectron spectroscopy (XPS) analysis was carried out to check what structural influence is exerted on the catalyst by sodium tungstate and a pyridine treatment. As a result, addition of pyridine to the silica ($SiO_2$) support does not affect the change in the binding energy of O 1s; however, the addition of $Na_2WO_4$ to the silica ($SiO_2$) support exhibited a phenomenon of a peak shift of −0.9 eV. Meanwhile, the addition of pyridine to the $Na_2WO_4/SiO_2$ catalyst resulted in a phenomenon of a peak shift of +0.4 eV (see Experimental Example 2 and FIG. 2A).

Furthermore, according to an Experimental Example of the present inventive concept, when the 2p binding energies of Mn, Na, and W in the catalyst for oxidative coupling of methane according to the present inventive concept was analyzed, it was confirmed that the peak of Mn 2p binding energy of the (PYD*)-Mn/$SiO_2$ catalyst appeared to be smaller than that of the Mn/$SiO_2$ catalyst, whereas in the case of catalysts having $Na_2WO_4$ supported thereon, all the peaks of Mn 2p binding energy increased (see Experimental Example 2 and FIG. 2B to FIG. 2D). These results imply that when the catalyst is treated with pyridine, the surface distribution and the surface density of Mn, Na, and W on the catalyst surface are increased, and as the degrees of contribution of Mn, Na, and W constituting an active phase in the oxidative coupling reaction of methane increases, these elements serve as an important element of increasing the methane conversion ratio and the C2 selectivity in the oxidative coupling reaction of methane. Consequently, it is suggested that the pyridine pretreatment according to the present inventive concept enables production of a catalyst for oxidative coupling of methane, which can have advantageous influence on the oxidative coupling reaction of methane.

According to another aspect of the present inventive concept, the present inventive concept provides a nitrogen-doped catalyst for oxidative coupling of methane including a silica ($SiO_2$) support; and sodium tungstate and manganese supported on the silica support as produced according to the above-described production method of the present inventive concept.

Regarding the catalyst for oxidative coupling of the present inventive concept, the nitrogen is derived from pyridine.

According to another aspect of the present inventive concept, the present inventive concept provides a method for an oxidative coupling reaction of methane, the method including a first step of packing a catalyst for oxidative coupling of methane produced according to the present inventive concept into a reactor; and a second step of introducing a mixed gas including methane, oxygen, and an inert gas into the inside of the reactor and performing an oxidative coupling reaction of methane. More particularly, methane and oxygen are introduced into the reactor at a composition ratio of 0.5:1 to 5:1, and as the composition ratio of methane/oxygen is larger, it is disadvantageous for the methane conversion ratio; however, the selectivity for hydrocarbons such as ethylene and ethane in the product increases. As the composition ratio of methane/oxygen is smaller, the conversion ratio of methane increases; however, the concentration of oxides (CO and $CO_2$) in the product increases, and disadvantage results are obtained for the selectivity of C2.

According to the method for an oxidative coupling reaction of methane of the present inventive concept, the internal temperature of the reactor is maintained at 600° C. to 800° C. In a case in which the reaction temperature is as high as 800° C. or higher, it is advantageous for the conversion of methane; however, the C2 selectivity for the product may be reduced, and inactivation caused by deterioration (sintering) of the catalyst may become serious. On the other hand, in a case in which the reaction temperature is low, that is, in a case in which the reaction temperature is lower than 600° C., the reaction hardly proceeds due to thermodynamic limitations, and even though the C2 selectivity of the product may be advantageous at a reaction temperature of 600° C. to 800° C., the methane conversion ratio is lowered.

According to an Experimental Example of the present inventive concept, the nitrogen-doped catalyst for oxidative coupling of methane ($Na_2WO_4$-(PYD*)-Mn/$SiO_2$) produced according to the Examples of the present inventive concept was subjected to a temperature programmed reduction (TPR) analysis, and a comparison was made for the tendencies for temperature-dependent reduction. As a result, it was confirmed that a peak appeared at 709° C., which is lower by about 10° C. compared to the hydrogen reduction temperature of the catalyst of Comparative Example 1 that was not doped with nitrogen. In the case of a metal catalyst, reduction at a low temperature is superior as the interaction of the catalytic metal oxides is higher, and as viewed from these results, the nitrogen-doped catalyst according to the present inventive concept can be considered to have an excellent degree of contribution of metal oxides and an excellent effect of promoting reaction activity, and to thereby make the reduction at a low temperature easier. Consequently, it is suggested that since the nitrogen-doped catalyst has an excellent effect of activating the reaction at a low temperature, in a case in which the catalyst is used for a low-temperature reaction, the effect of enhancing the catalytic performance is excellent, and as a result, the yield of the product can be increased.

As described above, the method for manufacturing a nitrogen-doped catalyst for oxidative coupling of methane and a nitrogen-doped catalyst for oxidative coupling of methane produced by this method can increase the surface distribution and surface density of catalyst components, increases oxygen vacancies of the catalyst to activate methane, and can consequently increase the methane conversion ratio and the selectivity for the C2 product in an oxidative coupling reaction of methane.

BRIEF DESCRIPTION OF THE DRAWINGS

FIG. 2A shows the O 1s binding energies of various catalysts; FIG. 2B shows the Mn 2p binding energy; FIG. 2C shows the Na 1s binding energy; FIG. 2D shows the W 4f binding energy; and FIG. 2E shows the N 1s spectra of a (PYD*)/$SiO_2$ catalyst, a (PYD*)-Mn/$SiO_2$ catalyst (Comparative Example 4), a $Na_2WO_4$-(PYD*)/$SiO_2$ catalyst (Comparative Example 5), and a $Na_2WO_4$-(PYD*)-Mn/$SiO_2$ catalyst (Example).

3B shows a TEM image and the results of HAADF and EDS mapping of a nitrogen-doped $Na_2WO_4$-(PYD*)-Mn/$SiO_2$ catalyst.

Figure 4:
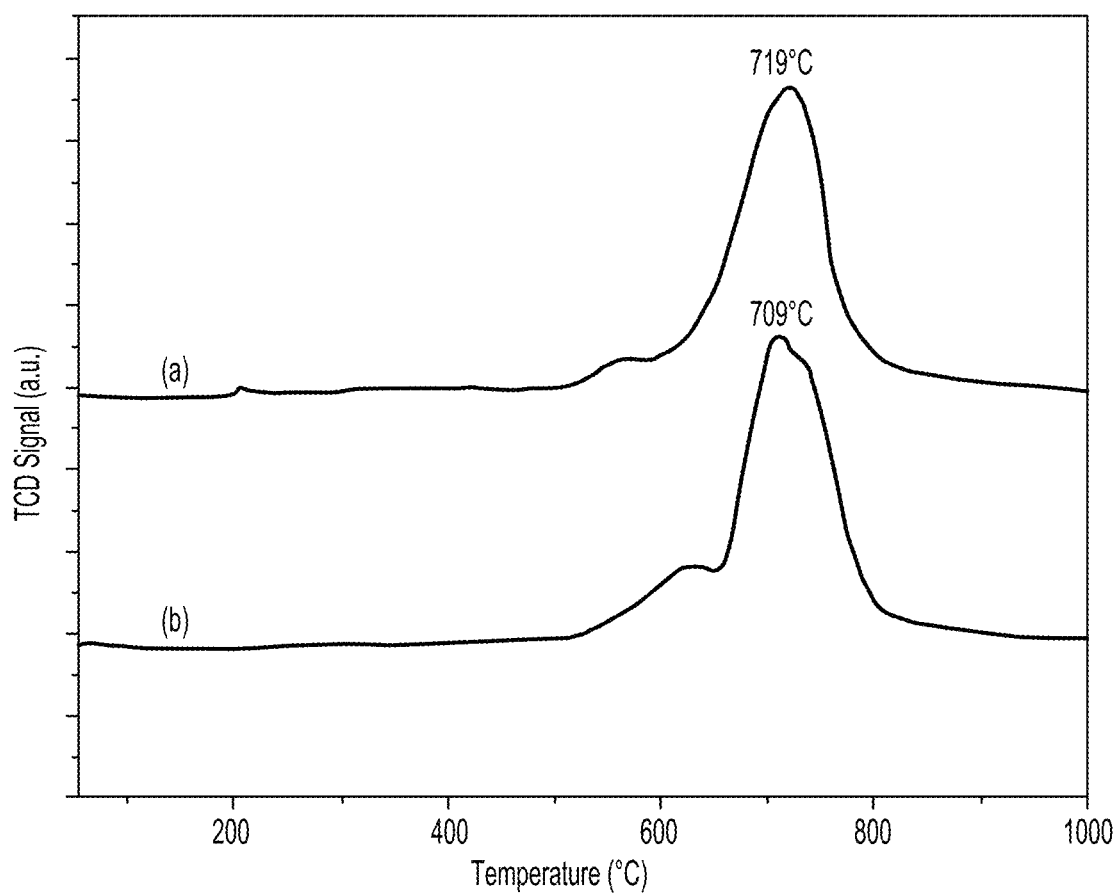

FIG. 4 is a chart showing the results of a temperature programmed reduction (TPR) analysis of the various catalysts.

DETAILED DESCRIPTION OF THE PREFERRED EMBODIMENTS

Hereinafter, the present inventive concept will be described in more detail by way of Examples. These Examples are intended only for illustrating the present inventive concept, and therefore, the scope of the present inventive concept is not construed to be limited by these Examples.

Example: Production of Nitrogen-Doped Catalyst for Oxidative Coupling of Methane A catalyst for oxidative coupling of methane was produced by doping (adding) nitrogen into a catalyst for oxidative coupling of methane using pyridine. Specific production steps and methods are as follows.

Step (1) Step of Preparing Amorphous Silica

In order to pulverize amorphous silica (amorphous $SiO_2$) uniformly and finely for the production of a uniform catalyst, amorphous silica was physically pulverized using a mortar, and a powder having a particle size of several ten nanometers (nm) to several micrometers (μm) was obtained.

Step (2) Step of Producing Mn/$SiO_2$ Catalyst

Manganese was added to the silica ($SiO_2$) that had been treated in step (1), and a Mn/$SiO_2$ catalyst was produced. Specifically, the silica ($SiO_2$) that had been uniformly pulverized in step (1) was transferred into an alumina crucible. Subsequently, in order to add manganese thereto, an aqueous solution of manganese was prepared by mixing 0.94 g of a manganese precursor ($Mn(NO_3)_2 \cdot 4H_2O$) with 7.5 ml of distilled water while considering that the silica ($SiO_2$) pore volume was 0.75 $cm^2$/g, and then the mixture was subjected to a sonication treatment for 5 minutes to allow the precursor to be thoroughly dissolved in the aqueous solution. The aqueous solution of the manganese precursor produced as described above was added dropwise to 10 g of $SiO_2$ that had been uniformly pulverized by the process of step (1), and then the mixture was thoroughly mixed with a glass rod. The entire amount of the aqueous solution of manganese was added and mixed by the method described above, and then the resulting mixture was dried for 12 hours in an oven at 120° C. so as to remove water.

Step (3) Step of Producing PYD-Mn/$SiO_2$ Catalyst

Pyridine (PYD) was added to the Mn/$SiO_2$ catalyst, and thus a PYD-Mn/$SiO_2$ catalyst was produced. Specifically, in order to add pyridine to the Mn/$SiO_2$ catalyst that had been dried in step (2), 0.5 ml of pyridine and 7 ml of ethanol were mixed, and the mixture was subjected to a sonication treatment for 5 minutes. The pyridine solution thus produced was added dropwise to the Mn/$SiO_2$ catalyst dried in step (2), and the mixture was thoroughly mixed with a glass rod. The entire amount of the pyridine solution was added and mixed by the method described above, and then the resulting mixture was dried for 12 hours in an oven at 120° C. so as to remove water.

Step (4) Step of Adding $Na_2WO_4$ to PYD-Mn/$SiO_2$ Catalyst

In order to add $Na_2WO_4$ to the pyridine-added Mn/$SiO_2$ catalyst (PYD-Mn/$SiO_2$) produced in step (3), 0.61 g of a $Na_2WO_4 \cdot 2H_2O$ precursor was dissolved in 7.5 ml of distilled water, and then the mixture was subjected to a sonication treatment for 5 minutes to produce an aqueous solution of $Na_2WO_4$. The aqueous solution of $Na_2WO_4$ thus produced was added dropwise to the PYD-Mn/$SiO_2$ catalyst, and then the mixture was mixed by stirring the mixture with a glass rod. The entire amount of the aqueous solution of $Na_2WO_4$ was added and mixed by the method described above, and then the resulting mixture was dried for 12 hours in an oven at 120° C. so as to remove water.

Step (5) Step of Calcining Nitrogen-Doped Catalyst for Oxidative Coupling of Methane at High Temperature The catalyst for oxidative coupling of methane produced by performing the processes from step (1) to step (4) in sequence was subjected to calcining for 5 hours at 800° C. in an air atmosphere, and thus the catalyst was completed (rate of temperature increase 10° C./min).

Comparative Example 1: Production of Catalyst for Oxidative Coupling of Methane that was not Doped with Nitrogen A $Na_2WO_4$/Mn/$SiO_2$ catalyst that was not doped with nitrogen, which is conventionally used as a catalyst for an oxidative coupling reaction of methane, was produced. Specific production steps and methods are as follows.

Step (1) Step of Producing Mn/$SiO_2$ Catalyst

Manganese was added to silica ($SiO_2$), and a Mn/$SiO_2$ catalyst was produced. Specifically, silica ($SiO_2$) that had been finely pulverized using a mortar in step (1) described above was transferred into an alumina crucible, and then the following aqueous solution of manganese was produced in order to add manganese to the silica. The aqueous solution of manganese was prepared by mixing 0.94 g of a manganese precursor ($Mn(NO_3)_2 \cdot 4H_2O$) in 7.5 ml of distilled water while considering that the silica ($SiO_2$) pore volume was 0.75 $cm^2$/g, and then the mixture was subjected to a sonication treatment for 5 minutes. The aqueous solution of manganese thus produced was added dropwise to 10 g of $SiO_2$ of step (1), and then the mixture was stirred with a glass rod. The entire amount of the aqueous solution of manganese was added and mixed by the method described above, and then the resulting mixture was dried for 12 hours in an oven at 120° C. so as to remove water.

Step (2) Step of Adding $Na_2WO_4$ to Mn/$SiO_2$ Catalyst

In order to add $Na_2WO_4$ to the Mn/$SiO_2$ catalyst that had been dried in step (2), 0.61 g of a $Na_2WO_4 \cdot 2H_2O$ precursor was mixed with 7.5 ml of distilled water, and then the mixture was subjected to a sonication treatment for 5 minutes. The aqueous solution of $Na_2WO_4$ thus produced was added dropwise to the Mn/SiO$_2$ catalyst, and then the mixture was mixed by stirring with a glass rod. The entire amount of the aqueous solution of Na$_2$WO$_4$ thus prepared was added and mixed by the method described above, and then the resulting mixture was dried for 12 hours in an oven at 120° C. in order to remove water.

Step (3) Step of Calcining Na$_2$WO$_4$/Mn/SiO$_2$ Catalyst

The catalyst produced by performing the above-described steps in sequence was subjected to calcination for 5 hours at 800° C. in air (rate of temperature increase 10° C./min).

Comparative Example 2: Production of Mn/SiO$_2$ Catalyst

A Mn/SiO$_2$ catalyst was produced in order to compare the respective effects of adding Mn and NaW to a catalyst. Silica (SiO$_2$) was transferred into an alumina crucible, and then an aqueous solution of manganese was produced in order to add manganese to the silica. The subsequent processes were carried out in the same manner as in step (2) of Comparative Example 1, and after the catalyst was dried for 12 hours in an oven at 120° C. in order to remove water, the catalyst was treated for calcining for 5 hours at 800° C. in air (rate of temperature increase 10° C./min).

Comparative Example 3: Production of Na$_2$WO$_4$/SiO$_2$ Catalyst

A NaW/SiO$_2$ catalyst was produced in order to compare the respective effects of adding Mn and NaW to a catalyst. For the production of a sodium tungstate precursor solution, 0.61 g of a Na$_2$WO$_4$.2H$_2$O precursor was mixed with 7.5 ml of distilled water, and then the mixture was subjected to a sonication treatment for 5 minutes. The aqueous solution of Na$_2$WO$_4$ thus produced was added dropwise to a porous silica (SiO$_2$) powder, and then the mixture was mixed by stirring with a glass rod. The entire amount of the precursor solution thus prepared was added to be supported on the catalyst, subsequently the resulting mixture was dried for 12 hours in an oven at 120° C. in order to remove water, and a calcination process was carried out for 5 hours at 800° C. in air (rate of temperature increase 10° C./min).

Comparative Example 4: Production of (PYD)-Mn/SiO$_2$ Catalyst

In order to investigate the effect of adding pyridine on a Mn/SiO$_2$ catalyst, pyridine was supported on the surface of a Mn/SiO$_2$ catalyst. The subsequent procedure of the production process was conducted similarly to that of Comparative Example 2, provided that a pyridine treatment process was carried out after drying of the Mn/SiO$_2$ catalyst. A pyridine solution was prepared by mixing 0.5 ml of pyridine and 7 ml of ethanol and then subjecting the mixture to a sonication treatment for 5 minutes. The pyridine solution thus produced was added dropwise to the dried Mn/SiO$_2$ catalyst, and then the mixture was mixed by stirring with a glass rod. The entire amount of the pyridine solution thus prepared was added and mixed by the method described above, and then the mixture was dried for 12 hours in an oven at 120° C. so as to remove water. The dried catalyst was subjected to a calcination process for 5 hours at 800° C. in air (rate of temperature increase 10° C./min).

Comparative Example 5: Production of Na$_2$WO$_4$—(PYD)/SiO$_2$ Catalyst

A catalyst was produced by a method similar to that of Comparative Example 3 described above, provided that in order to add pyridine to a dried Na$_2$WO$_4$/SiO$_2$ catalyst, 0.5 ml of pyridine and 7 ml of ethanol were mixed, and the mixture was subjected to a sonication treatment for 5 minutes. The pyridine solution thus produced was added dropwise to the dried Na$_2$WO$_4$/SiO$_2$ catalyst, and then the mixture was mixed by stirring with a glass rod. The entire amount of the pyridine solution was added and mixed by the method described above, subsequently the mixture was dried for 12 hours in an oven at 120° C. so as to remove water, and then a calcination process was carried out for 5 hours at 800° C. in an air atmosphere (rate of temperature increase 10° C./min).

The properties, dispersibility, interaction, and the like of the catalysts doped with nitrogen using pyridine, which had been produced in the above-described Examples, were analyzed, and an oxidative coupling reaction of methane was carried out using the nitrogen-added catalysts. Specific experimental methods are as follows.

Test Example 1: Structural Change in Catalyst Caused by Nitrogen Addition

In order to check the structures of the catalysts produced in Examples and Comparative Examples of the present inventive concept, an XRD analysis was carried out.

Figure 1:
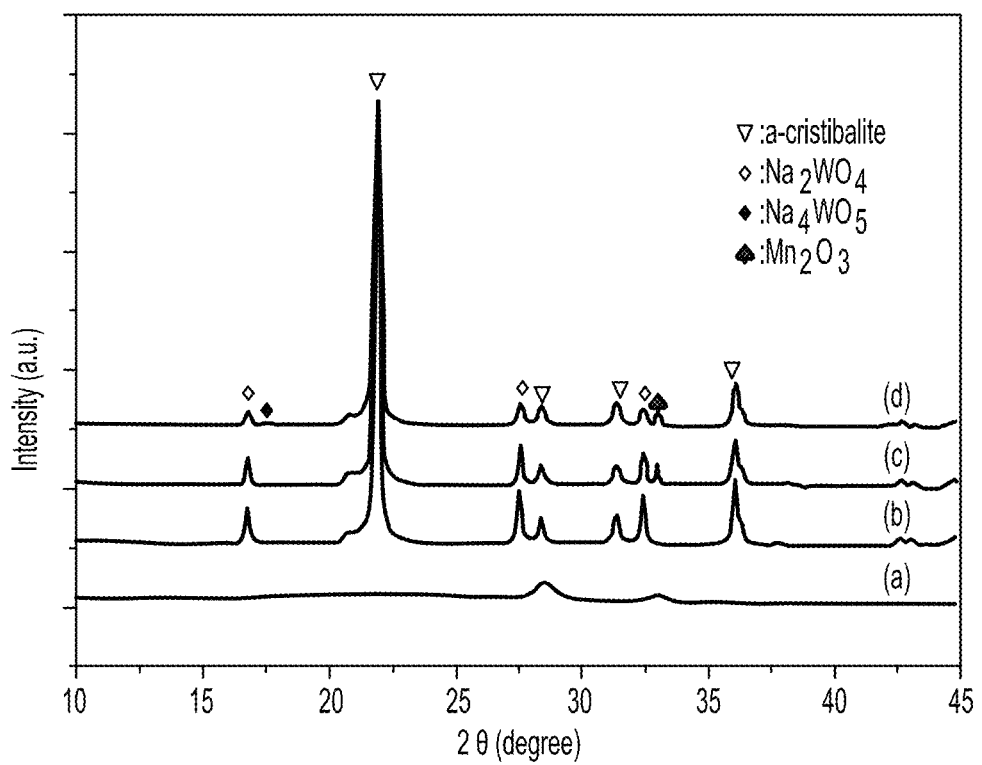
FIG. 1 is a chart showing the XRD analysis results for a Mn/$SiO_2$ catalyst ((a) in FIG. 1), a $Na_2WO_4/SiO_2$ catalyst ((b)), a $Na_2WO_4$/Mn/$SiO_2$ catalyst ((c)), and a $Na_2WO_4$-(PYD)-Mn/$SiO_2$ catalyst ((d)) according to Experimental Example 1.

FIG. 1(a) shows the XRD results for a Mn/SiO$_2$ catalyst. According to FIG. 1(a), broad peaks are seen, and the shape of the peaks is not clearly defined because the catalyst is supported on the surface of SiO$_2$ in an amorphous state. On the other hand, in the spectrum of FIG. 1(b) showing the XRD results of a Na$_2$WO$_4$/SiO$_2$ catalyst, a peak of α-cristobalite (2θ=22.0°) is recognized together with a Na$_2$WO$_4$ peak. This is because since a strong interaction between Na and Si occurs, amorphous silica (amorphous SiO$_2$) undergoes a phase change to the α-cristobalite phase during the calcination process at 800° C. In the XRD results for a Na$_2$WO$_4$/Mn/SiO$_2$ model catalyst (FIG. 1(c)), the α-cristobalite phase can be recognized similarly to the case of the Na$_2$WO$_4$/SiO$_2$ catalyst, and a peak for manganese supported on the surface of the catalyst can also be clearly recognized. In the case of a Na$_2$WO$_4$-(PYD)-Mn/SiO$_2$ catalyst obtained by subjecting a model catalyst to a pyridine treatment (FIG. 1(d)), unlike the case of the Na$_2$WO$_4$/Mn/SiO$_2$ catalyst, the appearance of a Na$_4$WO$_5$ peak can be seen at 2θ=17.5°. From these results, it is verified that a pyridine treatment can cause a change in the oxygen species in the metal oxide used as a catalyst.

Test Example 2: XPS Analysis for Catalyst After Nitrogen Addition

An XPS analysis was carried out for a silica (SiO$_2$) support, a pyridine-treated support ((PYD*)-SiO$_2$), a Mn-supported catalyst (Comparative Example 2; Mn/SiO$_2$), a pyridine-treated Mn catalyst (Comparative Example 4; (PYD*)-Mn/SiO$_2$), a NaW catalyst (Comparative Example 3; Na$_2$WO$_4$/SiO$_2$), a pyridine-treated NaW catalyst (Comparative Example 5; Na$_2$WO$_4$-(PYD*)-Mn/SiO$_2$), a model catalyst (Comparative Example 1; Na$_2$WO$_4$-Mn/SiO$_2$), and a pyridine-treated model catalyst (Example; Na$_2$WO$_4$-(PYD*)-Mn/SiO$_2$). The catalysts were treated in the same manner as in the production process for the model catalyst, that is, after supporting the catalytic substance, calcination was carried out for 5 hours at 800° C. in an air atmosphere, and then the analysis was performed.

Figure 2A:
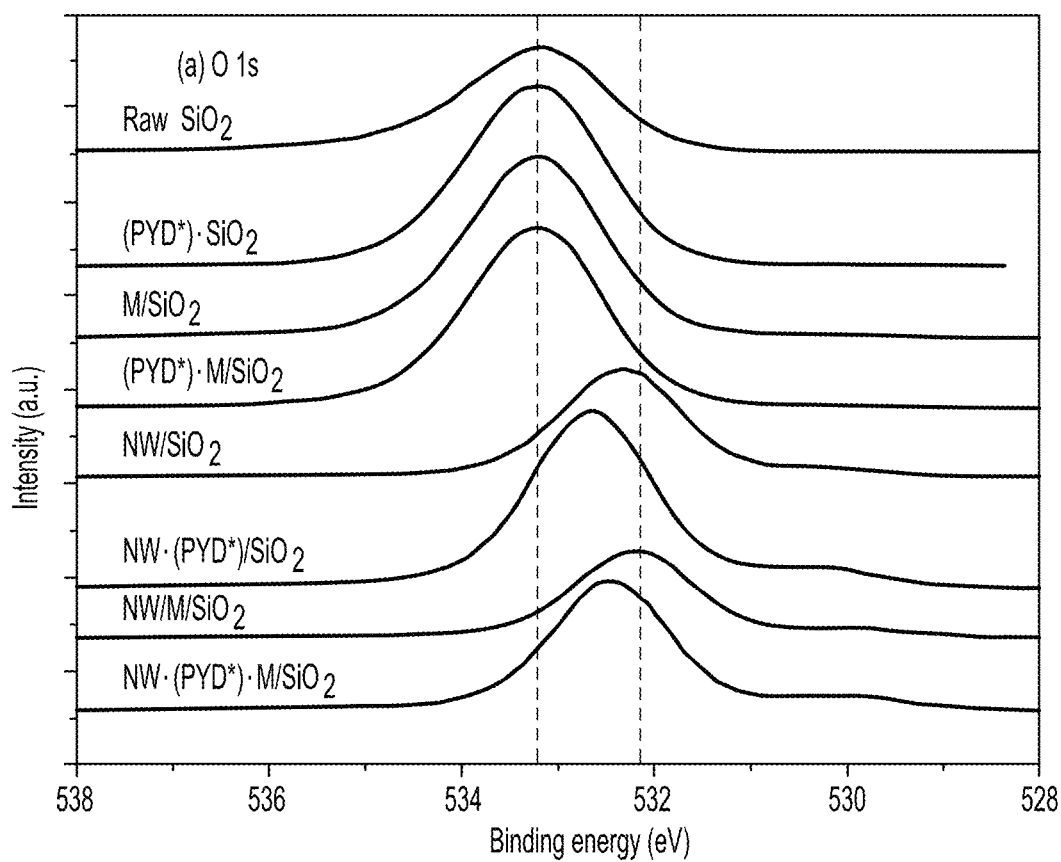
FIG. 2A to FIG. 2E are charts showing the results obtained by subjecting catalysts of different component to a pyridine treatment and then performing an XPS analysis according to Experimental Example 2.

FIG. 2A shows the O 1s binding energies of the various catalysts. The O 1s spectrum of untreated $SiO_2$ appeared at 533.2 eV, and the O 1s spectrum of (PYD*)-$SiO_2$ was also obtained similarly at 533.2 eV. The Si 2p binding energies of the Mn/$SiO_2$ catalyst and the (PYD*)-Mn/$SiO_2$ catalyst also appeared similarly at 533.2 eV. These results suggest that a pyridine treatment on an amorphous silica (amorphous $SiO_2$) support did not affect any change in the O 1s binding energy. On the other hand, the O 1s spectrum of the $Na_2WO_4$/$SiO_2$ catalyst appeared at 532.3 eV, and when this was compared with untreated $SiO_2$ (533.2 eV), a peak shift of −0.9 eV appeared. In this regard, it can be said that when $Na_2WO_4$ is added to amorphous silica (amorphous $SiO_2$), amorphous silica becomes crystalline with the α-cristobalite phase due to a strong interaction between Na and Si, and thus a shift in the O 1s binding energy occurs.

On the other hand, the O 1s spectrum of the pyridine-treated $Na_2WO_4$-(PYD*)/$SiO_2$ catalyst is at 532.7 eV, and when this was compared with the $Na_2WO_4$/$SiO_2$ catalyst that had not been treated with pyridine, a peak shift of +0.4 eV occurs. This is considered to be because while pyridine adsorbs to the OH— group at the $SiO_2$ surface, and the catalyst undergoes a heat treatment process, amorphous $SiO_2$ undergoes a phase change to the α-cristobalite phase due to an interaction between Na and Si, and the added pyridine has additional influence.

The O 1s spectrum of $Na_2WO_4$/Mn/$SiO_2$ is 532.2 eV, and when this is compared with simple $SiO_2$ (533.2 eV), a low shift of −1.0 eV appears. On the other hand, the O 1s spectrum of the pyridine-treated $Na_2WO_4$-(PYD*)-Mn/$SiO_2$ catalyst is 532.5 eV, and when this is compared with the O 1s spectrum of the $Na_2WO_4$/Mn/$SiO_2$ catalyst (532.2 eV), a peak shift of +0.3 eV occurs. These results suggest that as nitrogen is doped by a pyridine treatment, a change occurs in the O 1s binding energy.

Figure 2B:
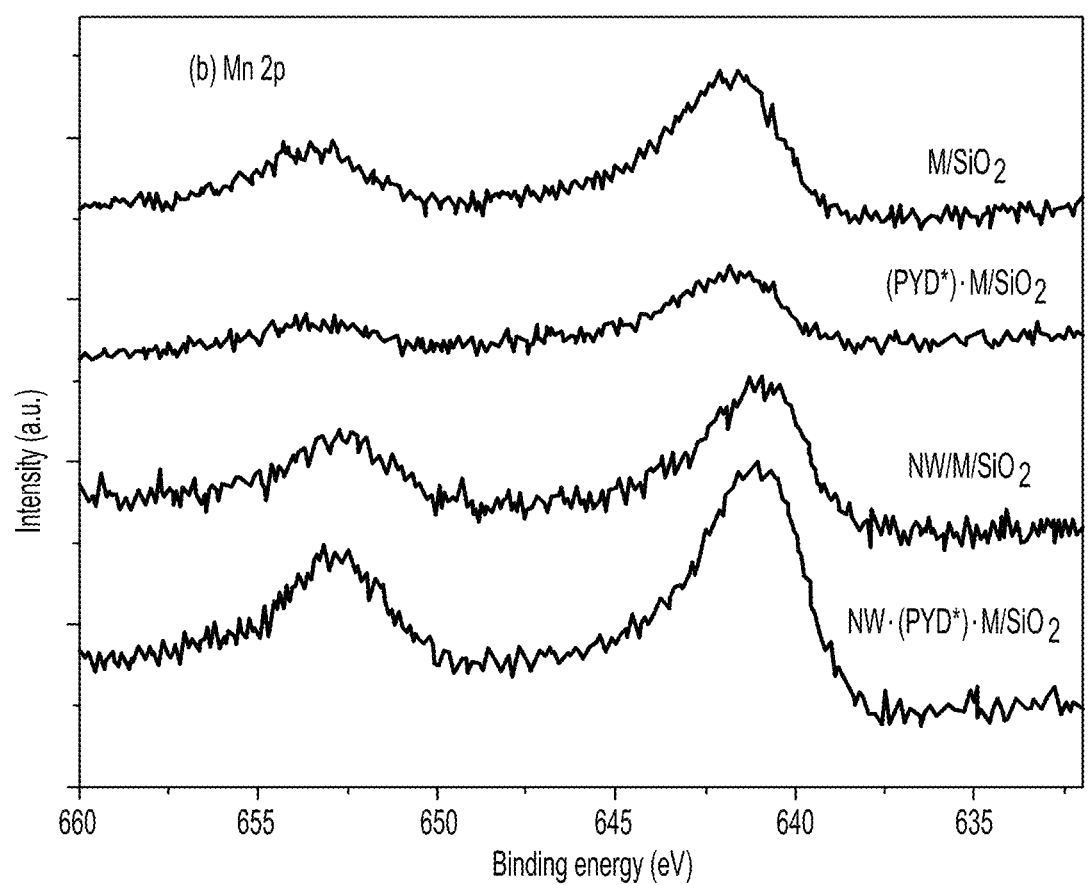
Figure 2C:
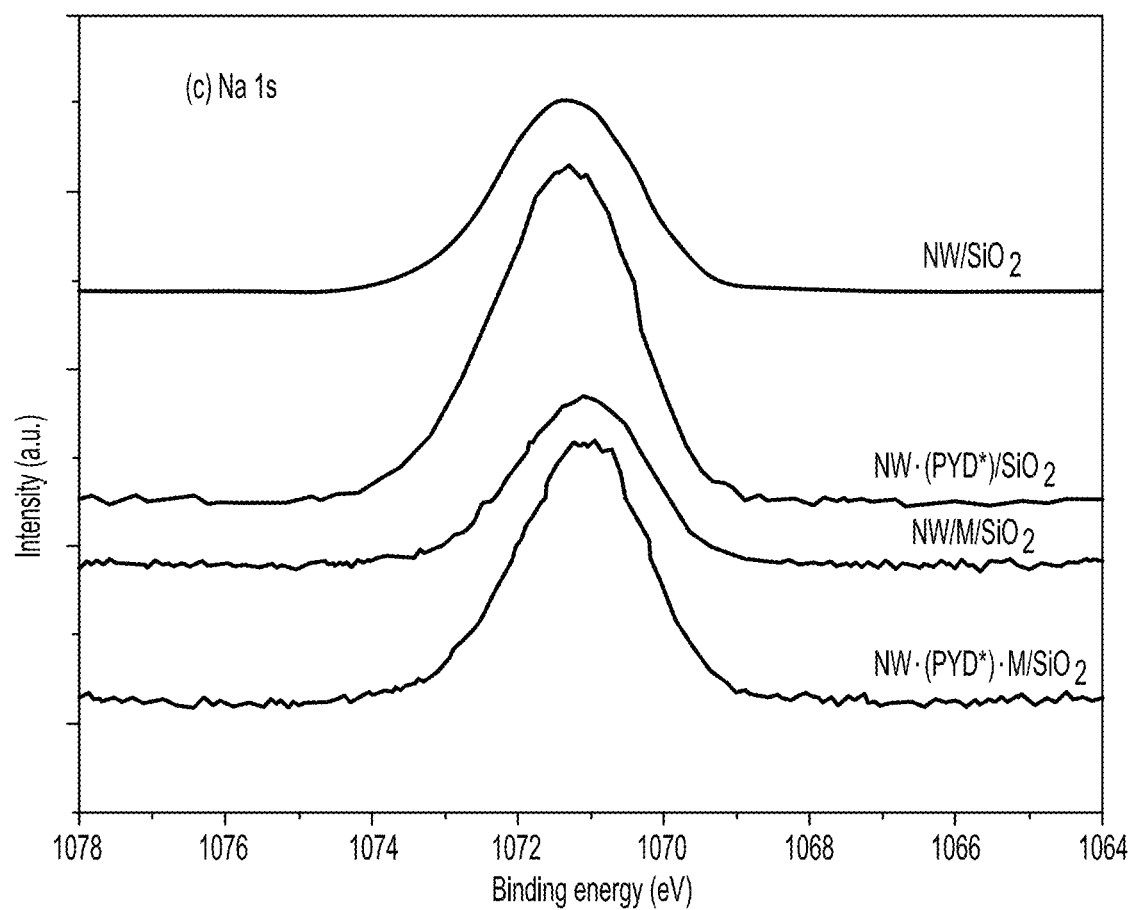
Figure 2D:
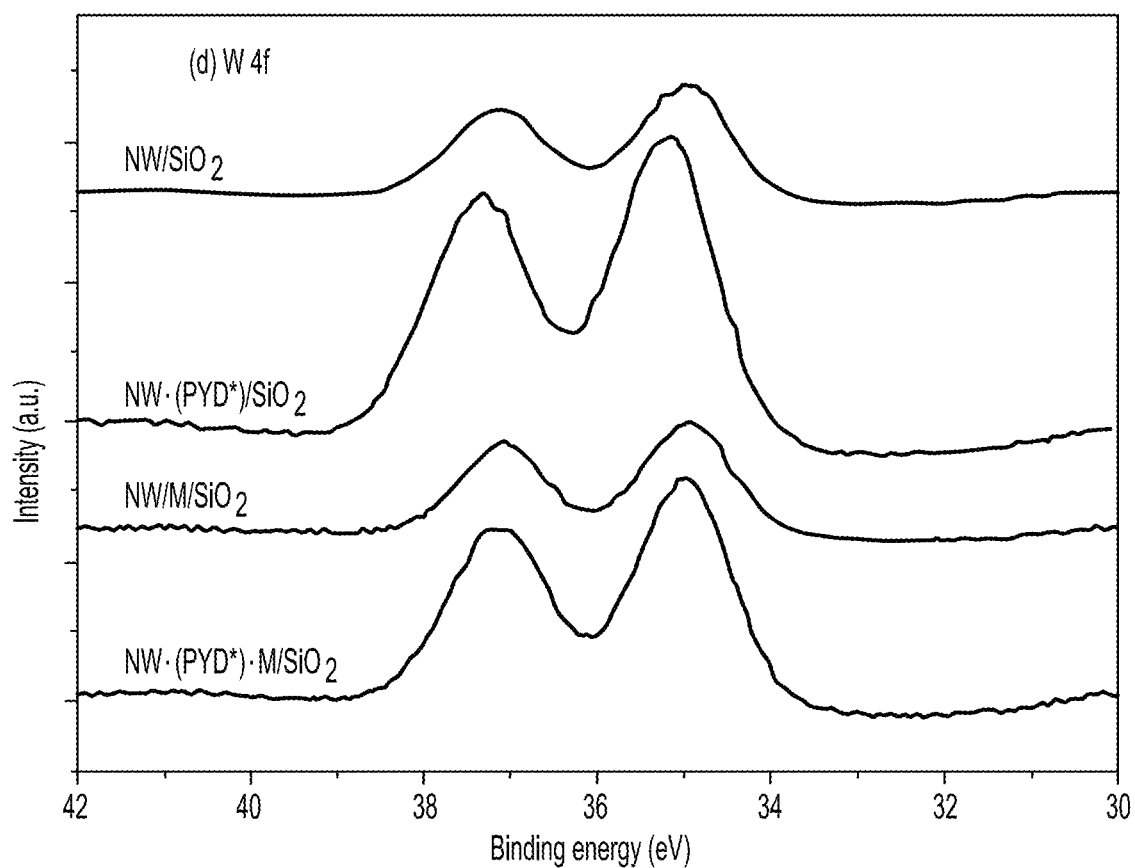

FIG. 2B shows the Mn 2p binding energy of Mn/$SiO_2$ (Comparative Example 2), (PYD*)-Mn/$SiO_2$ (Comparative Example 4), $Na_2WO_4$-Mn/$SiO_2$ (Comparative Example 1), and $Na_2WO_4$-(PYD*)-Mn/$SiO_2$ (Example). FIG. 2C shows the Na 1s binding energy of $Na_2WO_4$/$SiO_2$ (Comparative Example 3), $Na_2WO_4$-(PYD*)/$SiO_2$ (Comparative Example 5), $Na_2WO_4$-Mn/$SiO_2$ (Comparative Example 1), and $Na_2WO_4$-(PYD*)-Mn/$SiO_2$ (Example), and FIG. 2D shows the W 4f binding energy.

When the intensities of the Mn 2p spectra are compared in FIG. 2B, it can be seen that the intensity of the Mn 2p spectrum of the (PYD*)-Mn/$SiO_2$ catalyst is lower than that of the Mn/$SiO_2$ catalyst. However, in the cases of the catalysts having $Na_2WO_4$ supported thereon in FIG. 2B to FIG. 2D, it can be verified that the $SiO_2$ support acquires the α-cristobalite phase, and the intensities of Mn 2p (FIG. 2B), Na 1s (FIG. 2C), and W 4f (FIG. 2D) are all commonly increased by a pyridine treatment. This can be considered to be because the degrees of contribution of Mn, Na, and W on the catalyst surface is increased by a pyridine treatment. Since Mn, Na, W constitute a catalytically active phase in the oxidative coupling reaction of methane, when the densities of these elements at the surface are high, the elements serve as important factors for increasing the methane conversion ratio and the C2 selectivity in the oxidative coupling reaction of methane. Therefore, it is considered that the pyridine pretreatment process exerts an advantageous effect on the oxidative coupling reaction of methane.

Figure 2E:
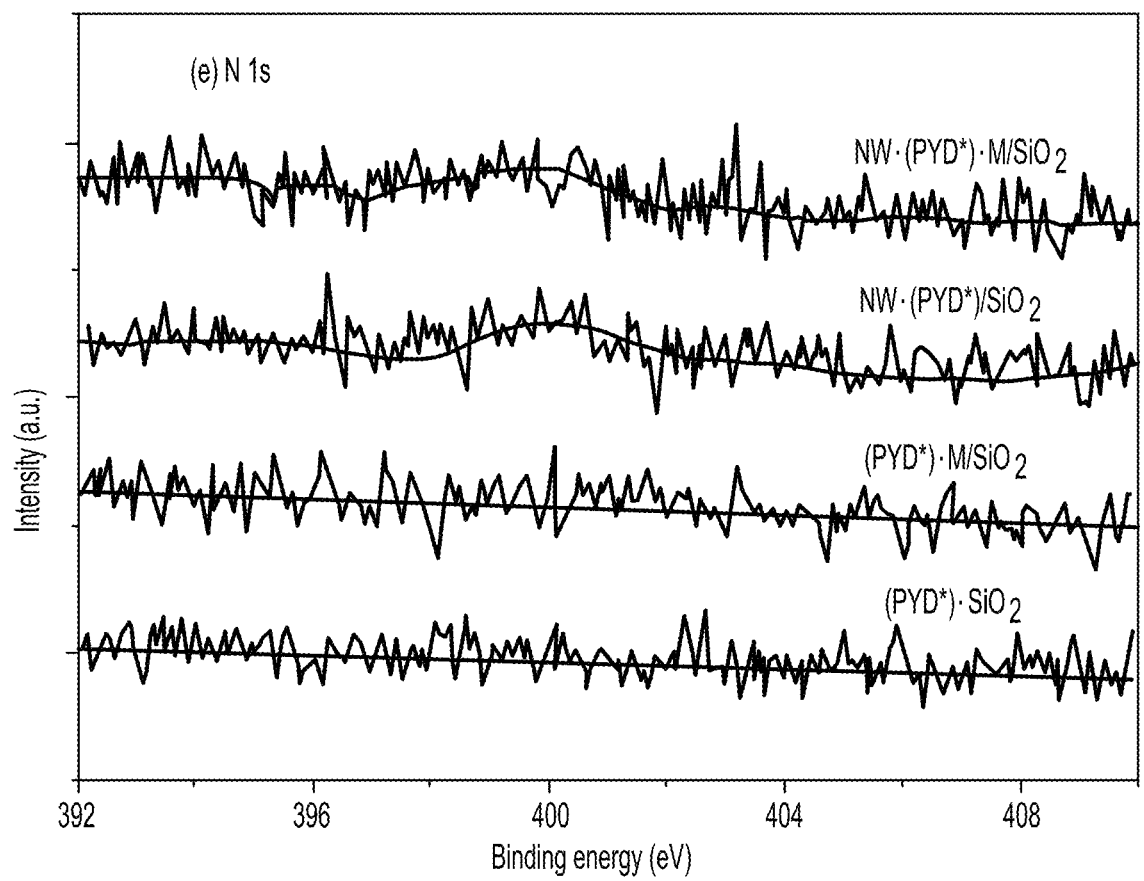

FIG. 2E shows the N 1s spectra of (PYD*)/$SiO_2$, (PYD*)-Mn/$SiO_2$ (Comparative Example 4), $Na_2WO_4$-(PYD*)/$SiO_2$ (Comparative Example 5), and $Na_2WO_4$-(PYD*)-Mn/$SiO_2$ (Example) catalysts. The results of an XPS analysis shows that the N 1s peaks of the (PYD*)/$SiO_2$ and (PYD*)-Mn/$SiO_2$ catalyst do not appear. However, in the cases of the $Na_2WO_4$-(PYD*)/$SiO_2$ and $Na_2WO_4$-(PYD*)-Mn/$SiO_2$ catalysts, it can be seen that the N 1s peak appears at 399.9 eV. This is considered to be because as pyridine is adsorbed to the amorphous silica ($SiO_2$) surface, and as the amorphous silica undergoes a phase change into the α-cristobalite phase due to an interaction between Na and Si, the nitrogen at the $SiO_2$ surface is substituted into the interior of the $SiO_2$ lattice.

Test Example 3: TEM and STEM/EDS Analysis of Catalyst After Nitrogen Addition

Figure 3A:
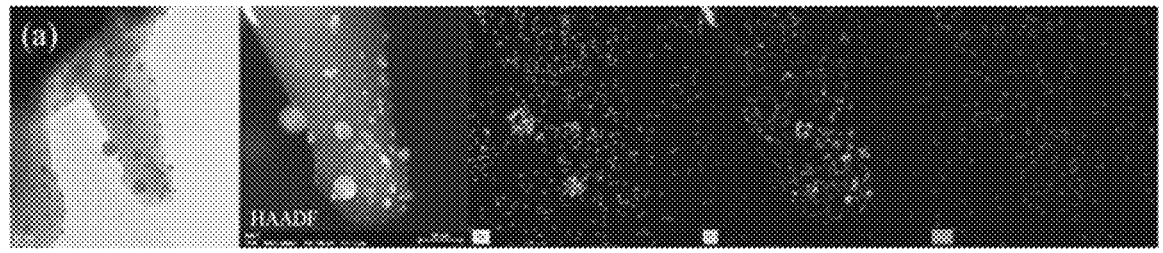
FIG. 3A shows a TEM image and the results of HAADF and EDS mapping of a $Na_2WO_4$-Mn/$SiO_2$ catalyst; and FIG.
Figure 3B:
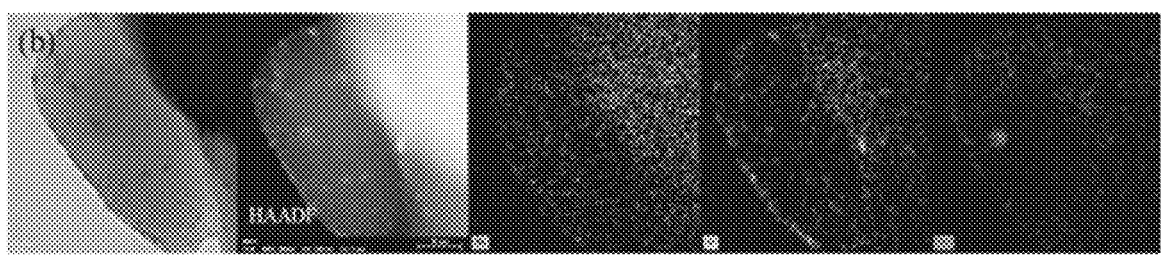

In order to check the surface state and the particle size of the catalyst and the dispersibility of the catalyst particles, TEM and STEM/EDS analyses were carried out. FIG. 3A shows a TEM image, HAADF, and EDS mapping of the $Na_2WO_4$-Mn/$SiO_2$ catalyst, and FIG. 3B shows a TEM image, HAADF, and EDS mapping of the pyridine-doped $Na_2WO_4$-(PYD*)-Mn/$SiO_2$ catalyst. When the results of FIG. 3B are compared with the results of FIG. 3A, it is implied that the concentration at the surface of the catalyst particles increased significantly. It could be verified from these results that the surface concentration of the metal oxides of the existing catalyst for oxidative coupling of methane is increased by a pyridine treatment, and the activity and long-term stability of the catalyst are increased.

Test Example 4: TPR Analysis of Catalyst After Nitrogen Addition

FIG. 4 shows the results of a temperature programmed reduction (TPR) analysis of the $Na_2WO_4$/Mn/$SiO_2$ and $Na_2WO_4$-(PYD*)-Mn/$SiO_2$ catalysts. From the TPR analysis results of the $Na_2WO_4$-Mn/$SiO_2$ catalyst (FIG. 4a), it was confirmed that a reduction peak appeared at 719° C. However, in the case of the pyridine-treated $Na_2WO_4$-(PYD*)-Mn/$SiO_2$ catalyst (FIG. 4b), it was confirmed that a reduction peak appeared at 709° C. It can be considered that these results were obtained because the pyridine-treated $Na_2WO_4$-(PYD*)-Mn/$SiO_2$ exhibited a higher degree of contribution and superior interaction of metal oxides as compared to the model catalyst $Na_2WO_4$-Mn-$SiO_2$.

What is claimed is:
1. A method for manufacturing a catalyst for oxidative coupling of methane, the method comprising:
    a first step of preparing amorphous silica (amorphous $SiO_2$) as a support;
    a second step of adding and mixing an aqueous solution of manganese into the silica of the first step and then drying the mixture to produce a catalyst having manganese (Mn) oxide supported on the silica;
    a third step of adding and mixing a pyridine solution into the catalyst of the second step and then drying the mixture to produce a catalyst having pyridine and manganese supported thereon;
    a fourth step of adding and mixing an aqueous solution of sodium tungstate into the catalyst of the third step and then drying the mixture to produce a catalyst having sodium tungstate, pyridine, and manganese supported thereon; and a fifth step of calcining the catalyst of the fourth step and obtaining a nitrogen-doped catalyst for oxidative coupling of methane.

2. The method for manufacturing a catalyst for oxidative coupling of methane according to claim 1,
wherein the aqueous solution of manganese of the second step is produced by dissolving a manganese precursor in distilled water and mixing the manganese precursor such that the mass ratio of manganese oxide in the catalyst for oxidative coupling of methane is 0.5 wt % to 5 wt %.

3. The method for manufacturing a catalyst for oxidative coupling of methane according to claim 1,
wherein the aqueous solution of pyridine of the third step is produced by mixing ethanol and pyridine at a volume ratio of 5 to 7:0.2 to 2.5.

4. The method for manufacturing a catalyst for oxidative coupling of methane according to claim 1,
wherein the aqueous solution of sodium tungstate of the fourth step is produced by dissolving a sodium tungstate precursor in distilled water and mixing the sodium tungstate precursor such that the mass ratio of sodium tungstate in the catalyst for oxidative coupling of methane is 2 wt % to 10 wt %.

5. The method for manufacturing a catalyst for oxidative coupling of methane according to claim 1,
wherein the drying in the second step to the fourth step is carried out for 12 to 24 hours at 100° C. to 120° C.

6. The method for manufacturing a catalyst for oxidative coupling of methane according to claim 1,
wherein the calcination of the fifth step is carried out by raising temperature to 750° C. to 900° C. at a rate of temperature increase of 10° C./min in an air or oxygen atmosphere and then maintaining the temperature for 4 to 6 hours.

\* \* \* \* \*